United States Patent [19]

Rudkin et al.

[11] Patent Number: 4,922,745
[45] Date of Patent: May 8, 1990

[54] FLUID TRANSDUCER

[76] Inventors: Mark J. Rudkin, 10 Delph Road, Wimborne, Dorset; David I. H. Atkinson, 6 Dollis Drive, Farnham, Surrey, both of England

[21] Appl. No.: 166,254

[22] Filed: Mar. 10, 1988

[30] Foreign Application Priority Data

Mar. 11, 1987 [GB] United Kingdom ............... 8705757

[51] Int. Cl.$^5$ ..................... G01N 9/34; G01N 11/16
[52] U.S. Cl. ........................................ 73/32 A; 73/54
[58] Field of Search ................ 73/32 A, 54, DIG. 1, 73/30; 310/370

[56] References Cited

U.S. PATENT DOCUMENTS

| | | | |
|---|---|---|---|
| 3,420,092 | 1/1969 | Dorsch | 73/32 A |
| 3,902,365 | 9/1975 | Knauth | 73/32 A |
| 4,217,774 | 8/1980 | Agar | 73/32 A |
| 4,558,588 | 12/1985 | Beaudoin et al. | 73/54 |
| 4,679,427 | 7/1987 | Kanda et al. | 73/54 |

OTHER PUBLICATIONS

R. M. Langdon, "Vibratory Process Control Transducers," *Marconi Review*, vol. 43, No. 218 (Third Quarter 1980), pp. 156–175.

Primary Examiner—John Chapman
Attorney, Agent, or Firm—Sanford J. Asman

[57] ABSTRACT

A transducer for measuring a parameter of a fluid, such as density or viscosity, comprises two generally parallel tines extending from a common yoke, forming a tuning fork adapted to be immersed in the fluid. The tines are excited to vibrate resonantly and in anti-phase by one or more piezo-electric exciting elements, which are housed in one or more cavities within the tines or the yoke. The vibrations are sensed by one or more similarly-housed piezo-electric sensing elements. The tines are shaped to enhance their sensitivity to the parameter to be measured: for example they are provided with re-entrant surfaces to enhance density sensitivity, or elongated in the direction in which they vibrate to enhance viscosity sensitivity.

12 Claims, 4 Drawing Sheets

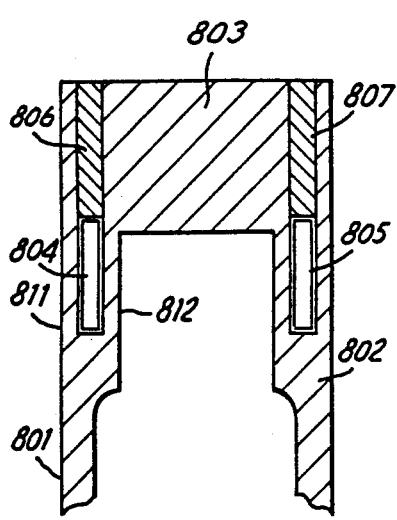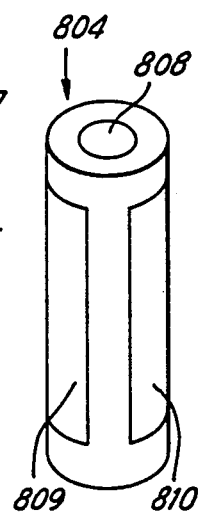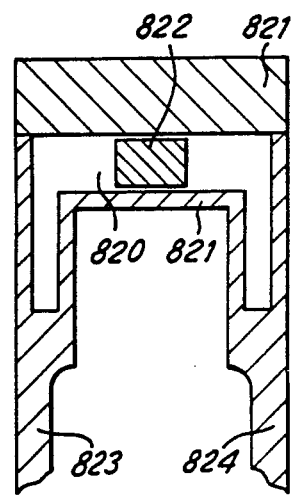
FIG.8　　FIG.9　　FIG.10
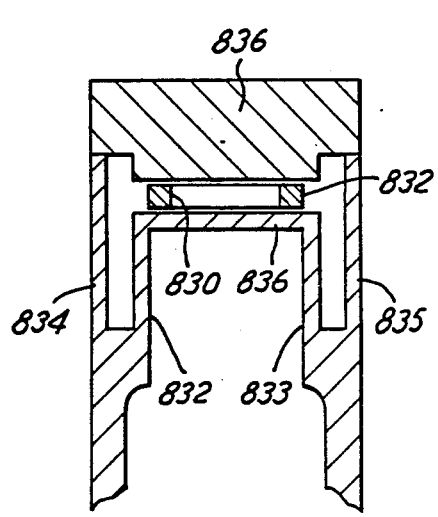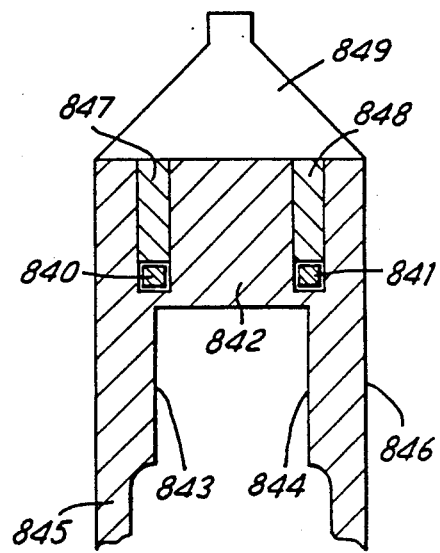
FIG.11　　FIG.12

FLUID TRANSDUCER

This invention relates to fluid transducers, and in particular to fluid transducers having a vibrating element sensor.

Such sensors measure parameters such as density and pressure by allowing them to influence a vibrating element and hence change its resonant frequency. This element is usually a tube resonating in a beam mode, or a cylinder resonating in a hoop mode. In all cases the vibration is monitored by sensing displacement or strain or a time derivative thereof and a drive system supplies an excitation force. Resonance in the chosen mode of vibration is maintained by closing the loop with a suitable feedback amplifier between the pick-up and drive. This amplifies the pick-up signal and applies it to the drive system with the correct phase.

The resonant frequency of the vibrating element may be mass loaded by the density of the fluid. The element appears to have increased its mass by an amount determined by the volume of the entrained fluid and so the resonant frequency is uniquely related to the density.

Descriptions of transducers which operate in accordance with these principles are to be found in United Kingdom Patent Specifications Nos. GB 1,264,317, GB 1,175,586 and GB 2,062,865.

An important application of transducers of this type is in the measurement of fluid parameters, for example in liquid flowing in a pipe line. It is therefore desirable that such transducers should disrupt flow as little as possible. Where the entire flow can be conveniently passed through a single tube transducer, little flow disruption occurs. Unfortunately the dimensions of a practical transducer are seldom large enough to accommodate all the flow without intolerable pressure drop and so there is often recourse to complex and undesirable flow dividers so that part of the flow may be diverted to a sampling transducer or the flow fully metered by a plurality of parallel transducers.

It is a known objective in the transducer art to provide a transducer that can meter a fluid with low flow disruption. Immersion transducers (that is transducers which are introduced into a body of fluid) are practical with vibrating cylinder sensors, but even these often cause unacceptable flow disruption, given the need for support of the element and its closely proximate excitation and pick up means which results in a structure often much bulkier than the vibrating tube itself.

According to the present invention, there is provided a fluid transducer comprising:

a sensing element adapted for immersion in a fluid, said sensing element comprising a pair of tines which extend from and are coupled together by a common yoke and which are resonantly vibratable at a common frequency but in antiphase;

means for exciting such resonant antiphase vibration of the tines; and means for sensing the frequency of the vibration; wherein the exciting means and the sensing means are contained within at least one cavity in the sensing element.

Preferably the exciting means is arranged to provide continuous excitation, advantageously at resonance.

A preferred embodiment of a fluid transducer in accordance with the present invention includes separate excitation and pick-up means in each of two tines, although single tine excitation and/or single tine pick-up are alternatives.

Advantageously, the exciting means and the sensing means are piezo-electric.

A fluid transducer in accordance with the present invention may be arranged as a densitometer by tine shaping to promote density sensitivity, preferably with a re-entrant surface such as a C-section or by means of a cavity adjacent a tine tip section.

In order that features and advantages of the present invention may be further appreciated, embodiments will now be described, by way of example only, with reference to the accompanying diagrammatic drawings, of which:

Figure 1:
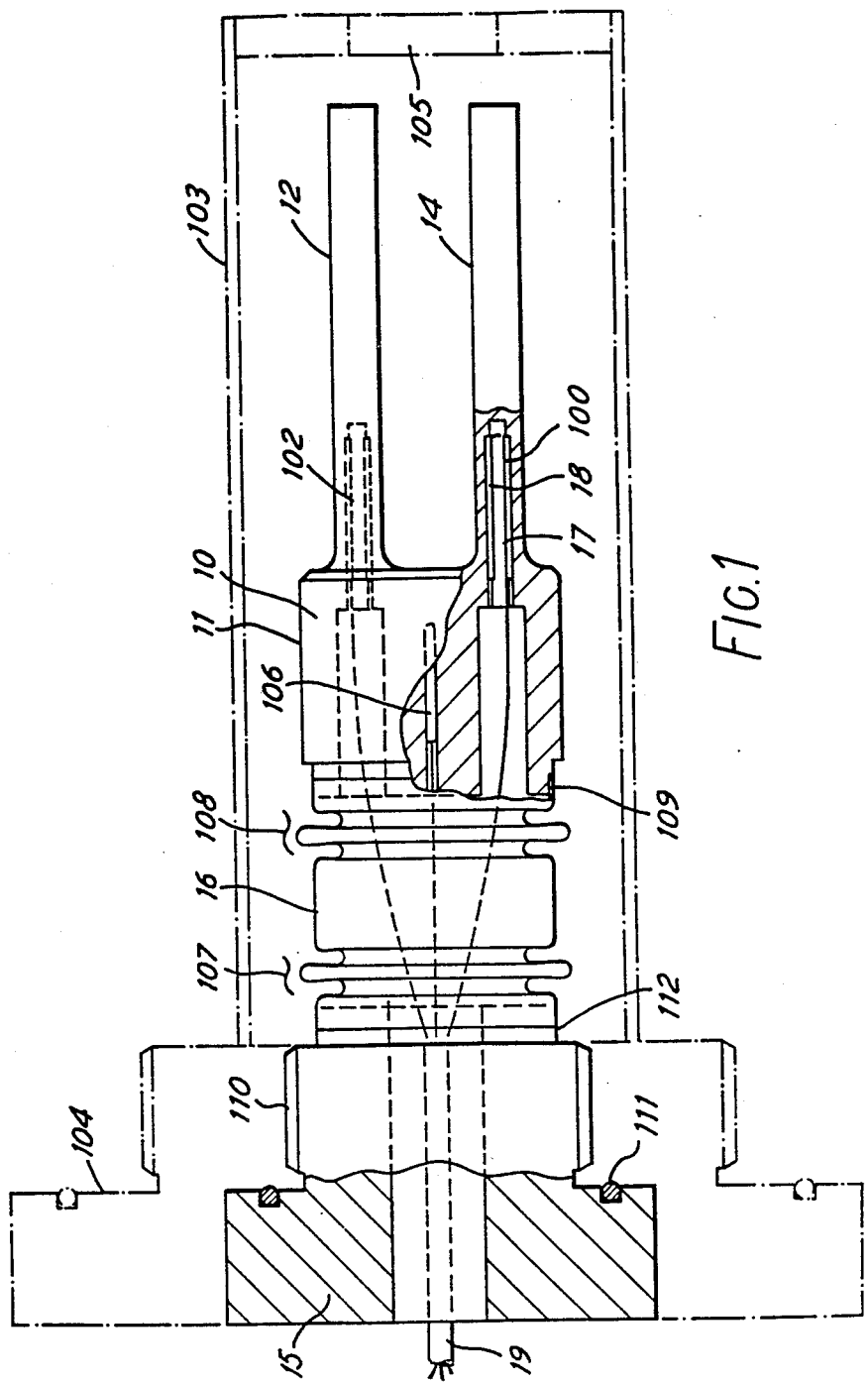
FIG. 1 is a part-sectional view of a fluid densitometer in accordance with the present invention.
Figure 3:
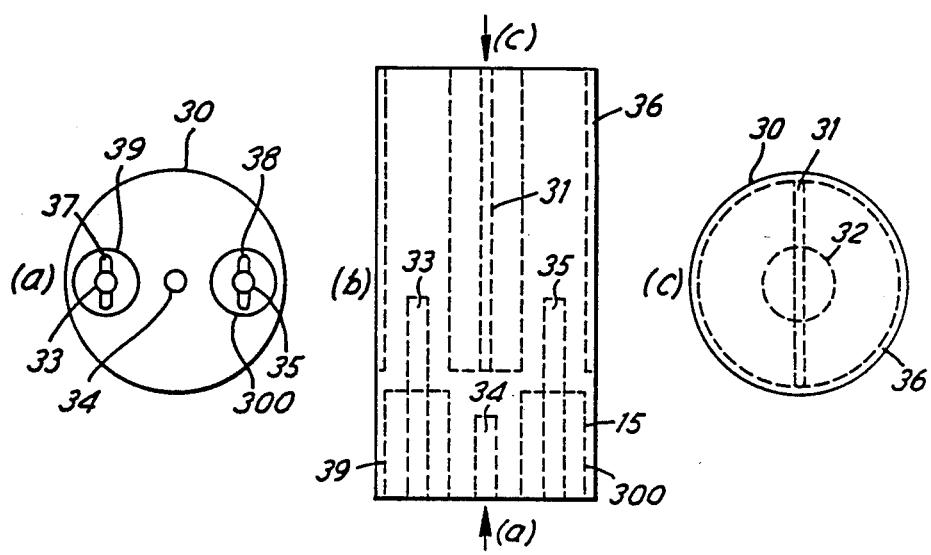
Figure 6:
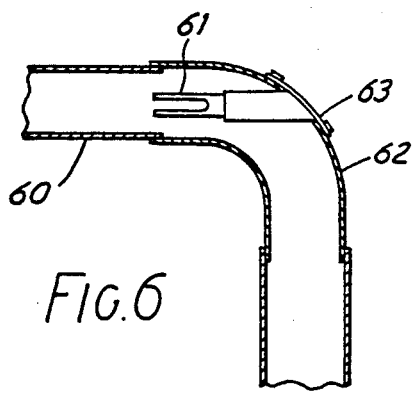
Figure 7:
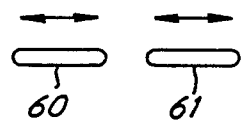
Figure 4:
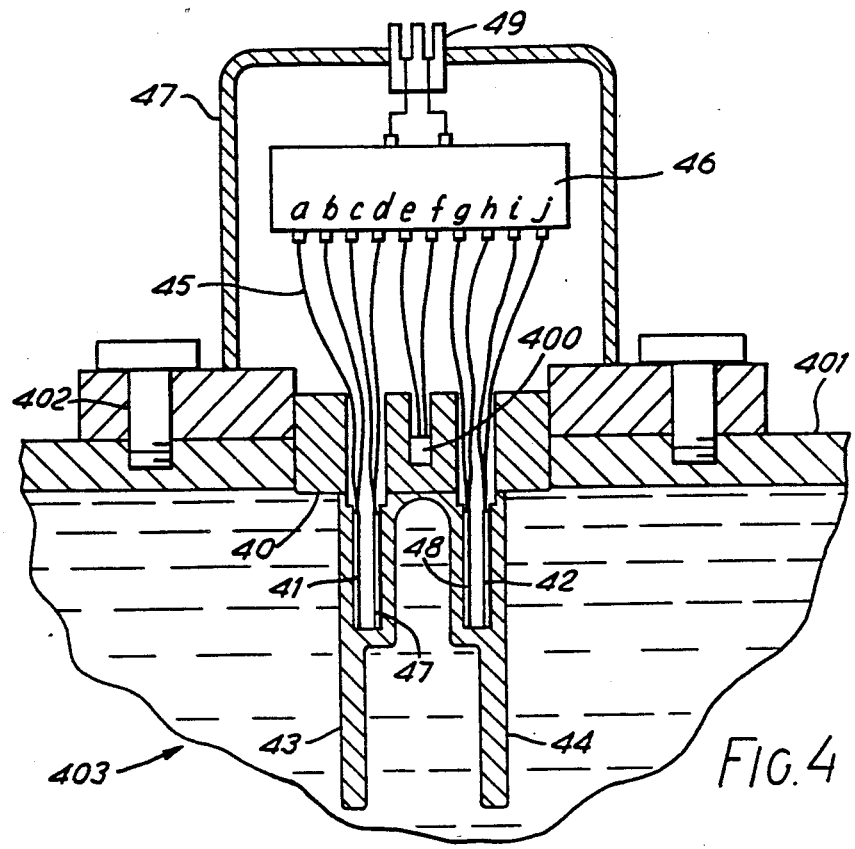
Figure 5:
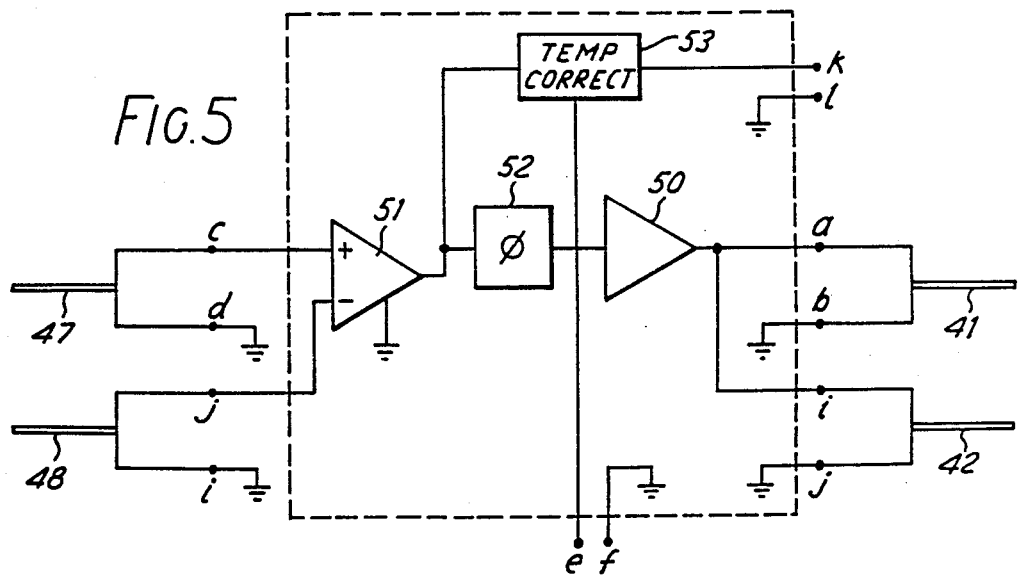

FIG. 3 (a)-(c) shows a construction schematic of the transducer of FIG. 1;

FIG. 4 shows a transducer in accordance with the present invention adapted for installation in a pipe;

FIG. 5 shows electronics associated with the transducer of FIG. 4;

FIG. 6 shows somewhat schematically an alternative mounting arrangement for a fluid transducer in accordance with the present invention;

FIG. 7 is a sectional view of fork tines of a viscometer in accordance with the present invention;

FIGS. 8 and 9 illustrate, again somewhat schematically, another fluid transducer in accordance with the present invention; and FIGS. 10 to 12 are schematic representations of yet further alternative embodiments of fluid transducers in accordance with the present invention.

In a fluid transducer 10 (FIG. 1), a fork sensing element comprises a yoke portion 11 and two vibratable tines 12, 14 extending therefrom in a substantially parallel relationship. Yoke portion 11 in addition to forming the fork base also serves provide support for the tines by connection to a support flange 15: connection is through the agency of a bellows 16, which provides vibration isolation of the fork with respect to the support flange 15.

Tine 14 has a cavity 17 formed in a root section thereof, to an inside surface of which a piezo-electric ceramic element 18 is affixed by bonding. Yoke 11, bellows 16 and support flange 15 have internal cavities (not shown in detail) so that a cluster of wires 19 may be provided internally, one pair of which are connected to the piezo-electric element 18, which may therefore be electrically excited to thereby excite vibration in the fork structure. A second piezo-electric element 20 is bonded on an adjacent surface of the cavity 17 and by means of electrical connection to this element a signal may be obtained which is representative of the vibration of the tine 14. Tine 12 has a cavity 21 in which two piezo-electric elements are similarly mounted to provide excitation and pick-up signals with respect to tine 12.

In operation, the transducer is arranged such that the tines are fully immersed in fluid to be metered. Vibration is excited by energising the two excitation piezo-electric elements, one within each tine, and the two pick-up piezo-electric elements, again one within each tine, yield a signal representative of the vibratory behaviour of the fork structure. The excitation of the tines is arranged such that the tine vibration is in opposed fundamental cantilever mode. This has the advantage that the vibration is balanced with no motion of the center of mass of the structure. Conversely enforced motion of the center mass, for example by external vibration has minimal effect on the vibration performance of the fork.

Figure 2:
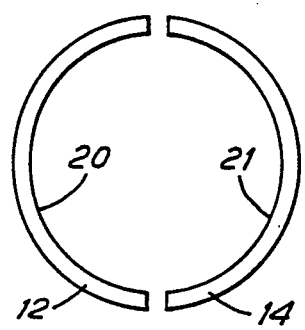
FIG. 2 is a sectional view of tines forming part of the densitometer of FIG. 1.

As the tines move, some of the surrounding liquid is displaced. The effective mass of the tines is increased by an amount determined by the volume of fluid entrained by the moving section; thus the effect is related to fluid density, and a densitometer is provided. Responsiveness to density change is greater as the amount of entrained fluid increases relative to the mass of the tines. To this end the tines 12 and 14 are of C section (FIG. 2) having re-entrant facing surfaces 20, 21 which serve both to increase the fluid entraining surface area and to reduce the sectional volume so that the tine carries more fluid with it, thereby increasing density sensitivity. Tines of other section such as 'D' section or simple bars may be employed, but sections with re-entrant surface are preferred. Where other sections are employed, the mass of moved fluid to tine mass ratio may be improved by making cavities, either closed or open, in the tine tip section.

An optional shroud 103 surrounds the fork element 10. Where shroud 103 is fitted, an extended support flange 104 is used. Shroud 103 is arranged such that it does not resonate over the frequency range of interest and may be for example of wire mesh construction to provide protection for the fork structure without disrupting flow too severely. Such protection may be important where foreign bodies within a metered fluid are likely to impact the tines.

Before the transducer of the embodiment described can be successfully used operationally, calibration will be required. Production transducers will normally be calibrated in at least one known liquid and in a sufficient volume thereof for substantially unbounded conditions to apply. In use, however, boundaries and barriers proximate the fork structure may be unavoidable, and the calibration will be invalid, since surfaces in the metered fluid near the transducer effectively increase the fluid added mass.

A transducer with an alternative form of shroud 103 provides a solution to the problem. Shroud 103 may be made by forming an essentially solid cylinder around the fork structure, the shroud 103 being rigidly attached to the support flange 104. An orifice 105 allows ingress and egress of the fluid to be metered. This form of shroud serves to define a known and repeatable boundary, and the fork transducer with its shroud may therefore be calibrated together, the calibration remaining valid even in the presence of boundaries proximate the region of metering.

Vibrating element transducers have a temperature characteristic dependent upon the Young's modulus variation of the material used with temperature and its thermal expansion. For a practical transducer, calibration against temperature is advantageous to compensate for temperature effects. To this end tuning fork transducer 10 has an internally mounted temperature sensor 106, to which electrical connection is made via wires in cluster 19.

The present invention provides a fluid transducer that may be relatively straightforwardly constructed. For metering of oil, for example the fork structure 10 may be machined from a cylinder 30 (FIG. 3) of metal 100 mm in length and 35 mm in diameter. Firstly outer surface portion 36 may be milled away to define the outer tine surface and yoke portion 15. A slot 31 may then be formed extending to a depth which determines the eventual length of the tines and across a diameter of the perforated end face (FIG. 3 (c), which represents a plan view of an end face of the cylinder 30). Slot 31 serves to establish separation between the tines.

A hole 32 may be drilled in the slotted end face and further holes 33, 34 and 35 may be drilled in the opposing face (FIG. 3 (a), which represents a plan view of the opposite end face of the cylinder 130). Holes 33 and 34, which extend to a depth overlapping slot 31, serve to establish cavities in the tine root sections for later introduction of the piezo-electric elements. Holes 33 and 35 are drilled to a larger bore (39, 300 respectively) effectively extending the tine root cavities at larger diameter. Hole 34 is adapted to receive a temperature sensor. Hole 32 serves to define a reentrant surface on the eventual tines, which will thereby be of 'D' section. Preferably hole 32 extends for the full length of the tines.

Piezo electric elements may now be bonded into position in holes 33 and 35 and a temperature sensor into hole 34, as may be appreciated from equivalent cavities 17, 102 and 106 (FIG. 1). Advantageously, holes 34 and 35 may be of more complex slotted shape 37, 38 (shown in outline in FIG. 3) to provide opposing flat surfaces in each cavity to which the piezo-electric elements may be bonded. Such more complex shapes may be formed by a process of spark erosion for the case of a metal fork.

Bellows 16 is formed as a thin walled cylinder, resilience being provided by virtue of two folded portions 107, 108. Bellows 16 is welded to yoke portion of transducer 10 around a mating circumference 109.

Support plate 15 (104, with the shroud) may be of any convenient shape and for example adapted to enter and seal with a tapping in a fluid pipe by virtue of threaded portion 110 and 'O' ring 111. Bellows 16 is welded thereto around a circumference 112. Shroud 103 (if fitted) is also welded. A cavity in support plate 15, the hollowness of bellows 16 and the extension of tine root cavities 17 and 102 provide an internal hollow which acts as a path for the placement of wires relaying electrical signals. The exit of wire cluster 19 may be sealed and the hollow filled with a known and inert gas, preventing internal corrosion and condensation of water, for example. Alternatively, the hollow may be evacuated.

The characteristic of the device thus far described which is exploited if the invention is arranged for example as a fluid density transducer is that of change of vibratory frequency (for example resonant frequency) with change of density of entrained fluid. In order to measure the frequency, several alternatives may be employed, one of which will now be described by way of example.

Vibration is excited by applying voltage to a piezo-electric device mounted at a point of high strain (when vibration is occurring) on a tine and removed from the natural axis, for example piezo element 18. Voltage application causes the piezo to apply and relax strain to the tine root by virtue of its contraction and bonding, which in turn excites vibration. Conversely, a piezo-electrical element bonded to a structure at a point of changing strain will generate a signal representative of strain variation which may be recovered. Thus once vibration has been established by driving the piezo-electric element, the drive could be removed and a signal recovered representative of the ensuing vibration. Alternatively a first piezo-electric element may be used to excite vibration, and a second used to recover the vibration signal. Similarly either a single element, or a separate drive element and a separate pick up element may be placed one in each tine. As an alternative to intermittent excitation, continuous excitation with either one or two elements and either one or two pick-ups may be employed.

In a preferred embodiment of the present invention (FIG. 4) a fluid density transducer 40 is subjected to continuous excitation by piezo-electric driver elements 41 and 42, mounted on outer surfaces in cavities in tines 43 and 44 respectively. Electrical connections, such as connection 45 of piezo-electric element 41 are established to an electronics board 46 contained within a housing 47. The connections are referenced as a to j. A function of the electronics board is to provide an excitation signal to elements 41 and 42 and accordingly these elements are connected in parallel and driven by a maintaining amplifier 50 (FIG. 5). The input signal for amplifier 50 is derived from piezo-electric pick-ups 47 and 48 respectively mounted in the cavities of tines 43 and 44. Signals from pick-ups 47 and 48 are connected respectively to the non-inverting and inverting input of a dual-input difference amplifier 51. It will be noted that since signals from the pick-ups are connected in opposing sense to inputs of opposite polarity, common mode noise will be rejected. The output of amplifier 51 is connected via a phasing circuit 52 to the input of the maintaining amplifier 50 to establish feedback between the excited and sensed vibration. The transducer 40 is thus maintained in continuous vibration. Phasing circuit 52 in the feed back path serves to ensure that the correct mode of vibration is sustained, as will be described in more detail below.

The output of input difference amplifier 51 is a periodic signal, representative of the frequency of vibration of the fluid transducer element. As previously described, the output is dependent upon temperature, and hence the signal is corrected for temperature by adding an offset 53 in response to a signal from a temperature sensor 400. The degree of correction applied is individually calibrated for each transducer. The corrected signal is relayed as an output signal k, for example via an external electrical connector 49. This signal (i.e. between k and 1) is thereby representative of the density of fluid by which the transducer is surrounded. Alternatively, an uncorrected signal may be output for relaying to external computation means storing correction and calibration values.

The feedback path via the input amplifier 51, phasing circuit 52 and maintaining amplifier 50 is arranged such that each tine 47, 48 of the transducer vibrates in its fundamental cantilever mode in a balanced way. The use of two drive elements and two pick-up eases the problem of ensuring that the element reliably enters the correct balanced mode of vibration. It has been found that this may be achieved by adjustment of the phasing circuit 52. The phasing circuit may also be adjusted to promote other vibration modes if required.

From the foregoing a number of advantages of the present invention will be appreciated.

Since the transducer presents a solid surface to the fluid to be measured, problems of contamination of the interior and potentially unreliable sealing arrangements for the electronics board are avoided. Furthermore, this solidity removes any dependence upon pressure of the fluid to be metered; which dependence is a characteristic of transducers of the hollow tube and cylinder type, where there are pressure effects due to internal and external pressure difference. Installation of the transducer is straightforward, being for example through a pipe or tank wall. Transducer 40 is adapted to be mounted in a wall 401 of a pipe by a securing flange 402. In some applications vibration isolation will not be required, and transducer 40 is directly welded to flange 402 offering a straightforward and highly secure construction.

Where foreign body impact or proximate surfaces are expected, an optional shroud may be fitted of appropriate type, as already described. Another circumstance where a shroud is of benefit is in intrinsically safe transducers, where the prevention of impact ensures that no large tine excursions can cause large and potentially dangerous voltages to be generated by the high impedance piezo-elements. Such a shrouded calibrated transducer may be adapted for use as a portable fluid meter, which may be used essentially as a dipstick since the structure is substantially insensitive to vibration that might be induced by hand held operation, by virtue of its balanced vibration.

A particular advantage of employing two pick-up elements is that the sensed signals may be connected so as to provide rejection of any common mode signals appearing during transmission.

A further important advantage of the present invention is the small section presented to flowing fluids. For example, the section presented by the transducer 40 to fluid flowing in pipe 401 in a direction 403 is only that of a single tine, which for oil might be typically $70 \times 2.5$ mm$^2$, as compared with an overall pipe cross sectional area of 80500 mm$^2$, leading to very little flow disturbance. A fork structure with tines of these dimensions formed in metal has a free air resonance at a frequency in the region of 1 KHz.

It will be appreciated that by mounting the fork structure turned through 90°, a yet smaller disruptive section may be presented. A preferred alternative when flow in a narrow base pipe 60 (approximately 50 mm diameter) is to be metered is mounting fork structure 61 in an elbow section 62 (FIG. 6). It will be realised that thereby a tine length which exceeds pipe diameter may be accommodated. The introduction of the fork structure into the flow path causes little significant extra pressure drop over and above that already caused by the elbow. An advantage is that elbow sections are often fitted with inspection plates for probe insertion, to which the transducer flange 63 may be readily adapted.

As the tines vibrate in a liquid, the tines drag through the fluid in shear. Vibration is therefore dependent upon the resistance to shear of the fluid, and hence its viscosity. Generally the tines of a densitometer may be designed to minimise viscosity effects by maximising entrained fluid volume with respect to drag, as in the 'C' section and hollow tines described above. As in many applications, metering over a small viscosity range only is required (e.g. typically $\pm 10$ Cp for oil), viscosity effects will be negligible. However, where larger viscosity variation is expected, extra corrections and calibrations may be advantageous.

The phase difference between the excitation signal and pick up signal generally increases with viscosity, hence by arranging that phasing circuit 52 acts to maintain a constant phase, viscosity sensitivity is reduced. Two modes of vibration, each exhibiting different density/frequency and viscosity/frequency characteristics may be excited, yielding simultaneous system equations from which viscosity may be eliminated. A detailed description of a two mode approach is to be found in the description of co-pending United Kingdom Patent Application No. 86 24339 (Publication No. 2182439). An alternative correction approach is to measure the amplitude of the vibration, which varies with viscosity as the Q of the system changes, as more damping is present with highly viscous liquids. Such correction has to be individually calibrated for each transducer.

A yet further possibility is to employ two transducers each exhibiting different density/frequency and vicosity/frequency characteristics.

In an alternative form of the present invention, tine section may be arranged to enhance viscosity sensitivity, thereby providing a liquid viscometer. Tine sections entraining a reduced volume but having a large surface area for drag are therefore advantageous. Tines 60 and 61 (FIG. 7) entrain little liquid, but are affected by drag (and hence viscosity) when vibrated in their plane of elongation. It will be appreciated, therefore, that a transducer having tines of such a section may provide a liquid viscometer analogous to the fluid desitometer described above.

In all the embodiments of the invention described so far, the piezo-electric exciting elements have been bonded within a cavity or cavities in the tines. However, it is possible to use piezo-electric exciting elements which are mounted in their cavity under a predetermined amount of compression. One way of achieving this is illustrated in FIGS. 8 and 9.

Thus in the transducer of FIG. 8, the upper ends of tines 801, 802 each have a cylindrical cavity machined therein from the top of yoke 803. Each recess contains a hollow cylindrical piezo-electric exciting element 804, 805, one of which is shown in more detail in FIG. 9. The elements 804, 805 are a tight fit radially in their respective cavities (i.e. they are of substantially the same diameter as their cavities), and they are held under a predetermined axial compression therein by respective plugs 806, 807 which screw into the cavities from the top of the yoke 803.

The piezo-electric element 804 of FIG. 9 has a first electrode extending over substantially the whole of its internal surface, and two further electrodes 809, 810 on diametrically opposed regions of its external surface. The electrodes 809, 810 are arranged to be disposed such that one is in the part of its cavity adjacent the outside face 811 of its tine 801 while the other is in the part of its cavity adjacent the inside face 812: both of the electrodes 809, 810 are insulated from the wall of the cavity. In operation, respective alternating voltages of 180° phase difference are applied to the electrodes 809, 810 with respect to the electrode 808. This has the effect of making one side of the element 804 try to expand while the other tries to contract, and vice versa, thus flexing the tine 801 from side to side and so causing it to vibrate: and the element 805 is similarly energized to cause the tine 802 to vibrate in anti-phase with the tine 801.

It is also possible to mount the piezo-electric exciting elements in the yoke of the transducer, rather than in the tines. Thus in the transducer of FIG. 10, a cylindrical cavity 820 is formed in yoke 821, and a piezo-electric element 822 in the form of a plate is mounted under a predetermined amount of compression in the cavity: this can be achieved by making the yoke in two separate pieces which are welded together to entrap the piezoelectric element. The piezo-electric element 822 is again insulated from the walls of its cavity 820, and it is symmetrically positioned in the cavity with respect to tines 823, 824. When an alternating voltage is applied to the plate 822, it alternately tries to expand and contract in a vertical direction (as viewed in FIG. 10), so tending to flex the lower surface of the yoke 821 and thus flex tires 823, 824 inwardly and outwardly, i.e. causing them to vibrate in anti-phase. The piezo-electric plate element 822 can be elongated perpendicularly to the line joining tines 823, 824, or in the direction of this line: both arrangements produce the desired anti-phase vibrations of the tines.

The transducer of FIG. 11 is somewhat similar to that of FIG. 10, except that the piezo-electric plate element of the FIG. 10 transducer is replaced by an annular piezo-electric element 830 coaxial with its cavity 832 (but still mounted under a predetermined amount of compression therein). The diameter of the element 830 is such that it passes through the regions of the cavity 831 closely adjacent the high-stress regions of yoke 836 where the inner faces 832, 833 of tines 834, 835 meet the yoke. Again, alternate expansion and contraction of element 830 in a vertical direction (as viewed in FIG. 11) causes the tines 834, 835 to vibrate in anti-phase.

Finally, in the transducer of FIG. 12, respective plate-like piezo-electrical exciting elements 840, 841 are provided in yoke 842 adjacent the high stress regions where the inner faces 843, 844 of tines 845, 846 meet the yoke. The elements 840, 841 are disposed in respective cavities drilled into yoke 842 from the top, and are held under a predetermined amount of compression by respective plugs 847, 848 screwed into these cavities from the top of yoke 842. Applying an alternating voltage to elements 840, 841 again causes tines 845, 846 to vibrate in anti-phase.

In all of the embodiments of FIGS. 8 to 12, the piezoelectric sensing element can be positioned in any convenient location within the tines or yoke where it will be flexed by, and thus sense, the vibrations of the tines. Further, these embodiments can all incorporate vibration isolation means of the form shown in FIG. 12, comprising a frusto-conical member 849 having its base welded to the top of the yoke and its narrower and secured, for example, in a flange member (or very short pipe section) adapted to be connected in flow series in a conduit carrying the fluid in which the transducer is to be immersed.

It will be appreciated that the transducers of FIGS. 8 to 12 all have appropriate passages for making electrical connections to the piezo-electric exciting and sensing means from the tops of their respective yokes: however, these passages have all been omitted in FIGS. 8 to 12, for the sake of simplicity.

We claim:
1. A fluid transducer comprising:
a sensing element adapted for immersion in a fluid, said sensing element comprising a pair of tines which extend from and are coupled together by a common yoke and which are resonantly vibratable at a common frequency but in antiphase;
means for exciting such resonant antiphase vibration of the tines; and
means for sensing the frequency of the vibration;
wherein the exciting means and the sensing means are both piezoelectric and both mounted under compression within at least one cavity in the sensing element, the tines have respective inner faces fac- ing towards each other, and at least the exciting means is mounted in a cavity in the yoke in a region thereof closely adjacent the point where the inner face of one of the tines joins the yoke.

2. A transducer as claimed in claim 1, wherein the exciting means is arranged to provide continuous excitation.

3. A transducer as claimed in claim 1, wherein said cavity is symmetrically positioned in said yoke with respect to the tines.

4. A transducer as claimed in claim 1, further including a shroud surrounding the sensing element.

5. A transducer as claimed in claim 1, further comprising mounting means for mounting the sensing element for immersion in the fluid, and vibration isolation means for isolating the sensing element from the mounting means.

6. A transducer as claimed in claim 5, wherein the vibration isolation means comprises a bellows.

7. A transducer as claimed in claim 5, wherein the vibration isolation means comprises a frusto-conical member having its base secured to said common yoke and its narrower end secured to said mounting means.

8. A transducer as claimed claim 1, wherein each tine is shaped to enhance the sensitivity of the sensing element to fluid density.

9. A transducer as claimed in claim 8, wherein each tine has a re-entrant surface facing in the direction of vibration.

10. A transducer as claimed in claim 1, wherein each tine is shaped to enhance the sensitivity of the sensing element to fluid viscosity.

11. A transducer as claimed in claim 10, wherein each tine has a generally elliptical cross-section, with the major axis of its elliptical section extending in the direction of vibration of the tine.

12. A transducer as claimed in claim 1, wherein the sensing means is mounted in a cavity in the yoke in a region thereof closely adjacent the point where the inner face of the other of said tines joins the yoke.

* * * * *